(12) United States Patent
Weissman et al.

(10) Patent No.: US 6,372,434 B1
(45) Date of Patent: Apr. 16, 2002

(54) METHODS FOR REDUCING THE COMPLEXITY OF DNA SEQUENCES

(75) Inventors: Sherman Weissman, New Haven; Roger Lasken, Guilford; Xinghua Pan, West Haven, all of CT (US)

(73) Assignee: Molecular Staging, Inc., New Haven, CT (US)

( * ) Notice: Subject to any disclaimer, the term of this patent is extended or adjusted under 35 U.S.C. 154(b) by 0 days.

(21) Appl. No.: 09/562,332

(22) Filed: May 1, 2000

Related U.S. Application Data

(62) Division of application No. 09/398,217, filed on Sep. 17, 1999.
(60) Provisional application No. 60/100,999, filed on Sep. 18, 1998.

(51) Int. Cl.[7] .......................... C12Q 1/68; C12P 19/34; C12N 1/00; C07H 21/02; C07H 21/04
(52) U.S. Cl. .................. 435/6; 435/91.1; 435/91.2; 435/875; 536/23.1; 536/24.3; 536/24.33; 935/76; 935/77; 935/78
(58) Field of Search ............... 435/6, 91.2, 875; 435/91.1; 536/23.1, 24.3, 24.33; 935/76, 77, 78

(56) References Cited

U.S. PATENT DOCUMENTS

| | | | |
|---|---|---|---|
| 5,556,750 A | 9/1996 | Modrich et al. | 435/6 |
| 5,854,033 A | * 12/1998 | Lizardi | 435/91.2 |
| 6,001,610 A | * 12/1999 | Seibl et al. | 435/91.2 |

OTHER PUBLICATIONS

Nelson, Nature Genetics (1993), vol. 4: 11–18.

Straus et al. "Genomic subtraction for cloning DNA corresponding to deletion mutations" Proc. Natl. Acad. Sci. vol. 87, pp. 1889–1893, Mar. 1990.

McAllister et al. "ERnrichment for Loci Identical–by Descent between pairs of Mouse or Human genomes by Genomic Mismatch Scanning" Genomics, vol. 47, pp. 7–11, Jan. 1998.

Cheung et al. "Genomic Mismatch Scanning: Applications to linkage and linkage disequilibrium analysis" Am. J. of Human Genetics, vol. 61, No. 4, Suppl. pp. A271, Oct. 1997.

Riley et al. "A novel, rapid method for the isolation of terminal sequences from YAC clones" Nucleic Acid Research, vol. 18, No. 10, pp. 2887–2890, 1990.

Prasher & Weissman Proc. Nat. Acad. USA (1996) 93: 659–663.

Geung et al. Nature Genetics (1998), 18: 225–230.

* cited by examiner

*Primary Examiner*—W. Gary Jones
*Assistant Examiner*—Arun kr. Chakrabarti
(74) *Attorney, Agent, or Firm*—Banner & Witcoff, Ltd.

(57) ABSTRACT

Genomic or cDNA, or fragments and mixtures thereof, can be screened by generation of subsets and then subjecting the subsets to mismatch scanning procedures. Alternatively, DNA fragments can be generated by cutting with a restriction endonuclease that generates variable overhangs. For either of the above methods, Y-shaped adapters having a region of non-complementary single-stranded DNA at the end can be used. Heterohybrid DNA, containing one DNA strand derived from each of two different samples, or homohybrids, containing DNA strands from the same sample, can be selected. Adapters attached to the ends of the fragments are designed to allow the selective isolation of homohybrid or heterohybrid DNA.

9 Claims, 2 Drawing Sheets

METHODS FOR REDUCING THE COMPLEXITY OF DNA SEQUENCES

This application is a divisional of U.S. Ser. No. 09/398,217, filed Sep. 17, 1999, still pending.

This application claims the benefit of application Ser. No. 60/100,999 filed Sep. 18, 1998.

TECHNICAL FIELD OF THE INVENTION

This invention relates to methods for reducing the complexity of DNA mixtures, subsequent analysis of genetic variations, and isolation of probes or clones of regions of interest.

BACKGROUND OF THE INVENTION

In 1993 Nelson and associates described a "genomic mismatch scanning" (GMS) method to directly identify identical-by-descent (IBD) sequences in yeast (Nelson, S. F., et al., *Nature Genetics*, 1993, 4:11–18; this and other papers, books and patents cited herein are expressly incorporated in their entireties by reference). The method allows DNA fragments from IBD regions between two relatives to be isolated based on their ability to form mismatch-free hybrid molecules. The method consists of digesting DNA fragments from two sources with a restriction endonuclease that produces protruding 3'-ends. The protruding 3'-ends provide some protection from exonuclease III (Exo III), which is used in later steps. The two sources are distinguished by methylating the DNA from only one source. Molecules from both sources are denatured and reannealed, resulting in the formation of four types of duplex molecules: homohybrids formed from strands derived from the same source and heterohybrids consisting of DNA strands from different sources. Heterohybrids can either be mismatch-free or contain base-pair mismatches, depending on the extent of identity of homologous regions.

Homohybrids are distinguished from heterohybrids by use of restriction endonucleases that cleave fully methylated or unmethylated GATC sites. Homohybrids are cleaved into smaller duplex molecules. Heterohybrids containing a mismatch are distinguished from mismatch-free molecules by use of the *E. coli* methyl-directed mismatch repair system. The combination of three proteins of the methyl-directed mismatch repair system MutS, MutL, and MutH (herein collectively called MutSLH) along with ATP introduce a single-strand nick on the unmethylated strand at GATC sites in duplexes that contain a mismatch (Welsh, et al., *J Biol. Chem.*, 1987, 262:15624). Heterohybrids that do not contain a mismatch are not nicked. All molecules are then subjected to digestion by Exo III, which can initiate digestion at a nick, a blunt end, or a recessed 3'-end, to produce single-stranded gaps. Only mismatch-free heterohybrids are not subject to attack by Exo III; all other molecules have single-stranded gaps introduced by the enzyme. Molecules with single-stranded regions are removed by absorption to benzoylated napthoylated DEAE cellulose. The remaining molecules consist of mismatch-free heterohybrids which may represent regions of IBD.

Nelson, et al., used *S. cerevisiae* hybrids as a model system and showed that sequences shared by two independently generated hybrids from the same parent strains could be identified in many instances. Experiments of this kind are much easier to do in yeast than in humans. The yeast genome is 250 times simpler than the human genome, it contains far fewer repetitive sequences, and genomic sequences of two yeast strains differ more than genomes of unrelated humans.

It has thus far not been possible to do comparable experiments with human genomic DNA In order to do so one needs to use methods to reproducibly generate simplified but highly polymorphic representations of the human genome. Pooling techniques based on mathematical principles are also essential to identify IBD sequences as well as other sequences showing allele frequency differences (AFD) (Shaw, S. H., et al., *Genome Research*, Cold Spring Harbor Laboratory Press, 1998, 8:111–123).

The human genome is enormously long, at $3 \times 10^9$ base pairs, and it is far too complex for efficient reannealing of homologous DNA strands after denaturation. The rate of annealing of a mixture of nucleic acid fragments in liquid phase is inversely proportional to the square of their complexity. Efforts have therefore been made to generate simplified representations of the genome for genetic methods based on cross hybridization of homologous sequences from different genomes. The exact degree of simplification of human genomic DNA needed to achieve efficient annealing depends on the conditions of hybridization including total DNA concentration, hybridization buffer, and temperature. In general a 10–100 fold simplification is needed for efficient annealing to occur at high DNA concentrations in high salt aqueous solutions (Lisitsyn, N. A., et al., *Science*, 1993, 259:946–951).

In some embodiments of the invention, DNA sequences of interest are replicated in rolling circle amplification reactions (RCA). RCA is an isothermal amplification reaction in which a DNA polymerase extends a primer on a circular template (Kornberg, A. and Baker, T. A, *DNA Replication*, W. H. Freeman, New York, 1991). The product consists of tandemly linked copies of the complementary sequence of the template. RCA can be used as a DNA amplification method (Fire, A. and Si-Qun Xu, *Proc. Natl. Acad Sci. USA*, 1991, 92:4641–4645; Lui, D., et al. *J Am. Chem. Soc.*, 1995, 118:1587–1594; Lizardi, P. M., et al., *Nature Genetics*, 1998, 19:225–232). RCA can also be used in a detection method using a probe called a "padlock probe" (Nilsson, M., et al., *Nature Genetics*, 1997, 16:252–255).

It would be useful to have superior ways of analyzing human DNA and other complex DNA samples.

SUMMARY OF THE INVENTION

A general method for screening genomic or cDNA, or fragments and mixtures thereof, involves sample simplification by the generation of subsets and then subjecting the subsets to mismatch scanning procedures. Any given DNA sequence will be represented in one and only one subset, minimizing the number of subsets required to detect a sequence of interest and guaranteeing that all possible sequences can potentially be covered by analyzing all possible subsets. The complexity of DNA sequences is reduced by attaching adapters to the ends of DNA fragments that allow the specific subsets of DNA to be selected and amplified. In some procedures, subsets are generated by replicating DNA in a polymerase chain reaction (PCR) or single primer extension reactions using primers that are complementary to sequences in the adapter and which, at the 3'-end, are complementary to a subset of sequences in the genomic or cDNA In another version of this method, DNA fragments are generated by cutting with a restriction endonuclease, such as Bsl1, that generates variable overhangs for which some of the nucleotides can have any of 2 to 4 of the bases A, C, G, or T. In this case, subsets are generated by ligating adapters to the fragment ends that have a specific sequence in the overhang and a primer binding site unique for each adapter. For either of the above methods, Y-shaped adapters can be used having a region of non-complementary single-stranded DNA at the end. Therefore, following ligation, the DNA fragment-plus-adapter construct has the non-complementary region at its ends. Use of Y-shaped adapters make it possible to generate non-overlapping subsets such that a given DNA fragment will only be represented in one of the possible subsets.

Procedures are given for isolating selected subsets from other, contaminating DNAs by using primers that have attached chemical moieties that can be captured on beads, columns, and the like. In some cases, the DNA is then released by cutting specifically designed sequences in the primers with restriction endonucleases. Fragment DNA is protected from these restriction endonucleases by methylation. The DNA subsets obtained are sufficiently reduced in complexity to allow improved analysis of sequence polymorphism by mismatch scanning procedures. Procedures are given for selecting DNA fragments representing regions of low polymorphism or for generating fragments depleted for regions of low polymorphism.

In some embodiments, the DNA fragments are replicated in a rolling circle amplification procedure (RCA, see reviews by Hingorani, M. M., and O'Donnell, M., *Current Biology*, 1998, 8:R83–86 and by Kelman, Z., et al., *Structure*, 1998, 6:121–5). The DNA polymerase III holoenzyme (hereafter sometimes denoted DNA pol III) is used in most of these methods to increase the rate and processivity of primer extension. DNA pol III also improves the ability to replicate through a DNA region of high GC content or other obstructions that tend to block DNA polymerases.

A method is also given for selecting heterohybrid DNA that contains one DNA strand derived from each of two different samples or homohybrids in which the DNA strands from different samples have not been recombined. Each DNA sample may consist of some concentration of a unique DNA fragment, or a mixture of fragments, and each sample may be derived from a single individual or more than one individual. The different DNA samples are mixed together, denatured, and then reannealed. Some of the DNA strands will reanneal back together with another strand from the same DNA sample forming a homohybrid. Other DNA strands will reanneal with a DNA strand from a different sample forming a heterohybrid. Adapters attached to the ends of the fragments are designed to allow the selective isolation of homohybrid or heterohybrid DNA. In one method, restriction endonuclease recognition sites are present in the adapters such that homohybrid or heterohybrid DNA can be selectively eliminated depending on the ability of the restriction endonuclease to cut the DNA.

DETAILED DESCRIPTION OF THE INVENTION

This invention provides for the screening of complex DNA preparations, including complex DNA comprised of genomic segments or cDNAs, and the isolation of genes without requiring prior knowledge of their biochemical function or map position. Methods of the invention divide DNA into subsets and then manipulate the subsets using a mismatch repair system and capture techniques to obtain specific DNA sequences, including genomic subsets of long genomic DNA generated by selective amplification of sequences exhibiting low polymorphism.

As used herein, "polymorphism" refers to genetic sequence variation between different individuals of a species. A "homoduplex" is double-stranded DNA where both strands derive from the same genome or pools of genome samples, and a "heteroduplex" is double-stranded DNA where each strand originated from different genomes or different pools of genomes. By "perfectly matched" is meant double-stranded DNA where each base residue is correctly paired with a base on the opposite strand, i.e., A to T and C to G. By "mismatched" is meant double-stranded DNA where at least one base residue on either strand is either not paired with any residue, or paired with an incorrect base, i.e., A not paired with T, C not paired with G.

In a typical practice of a method of the invention, at least one DNA sample is methylated, usually at the GATC sites with bacterial DAM methylase, and the sample is then cut with an enzyme that makes infrequent cuts such as Pvu1 (Nelson, S. F., et al., cited above). Any type of DNA sample may be subjected to methods of the invention, including genomic DNA, genomic fragments, cDNA, cDNA fragments, and mixtures of any of these. It is an advantage of the invention that it can be used to identify identical-by-descent sequences of low polymorphism in complex human or other genomic DNA samples. It can also be used to identify sequences of high polymorphism.

Figure 1A:
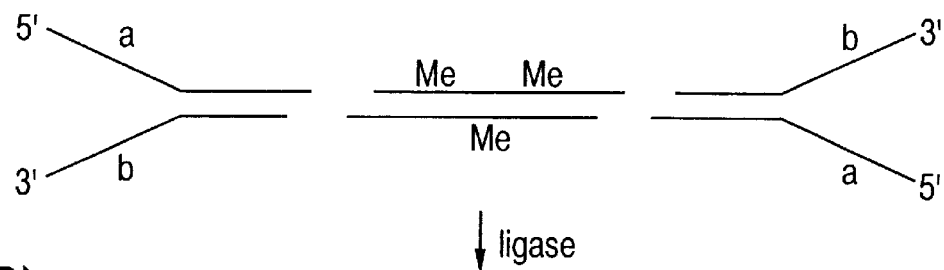
In FIG. 1A and FIG. 1B), Y-shaped adapters having non-complementary sequences on one end and appropriate overhangs for ligation on the other end are ligated to DNA fragments.
Figure 1B:
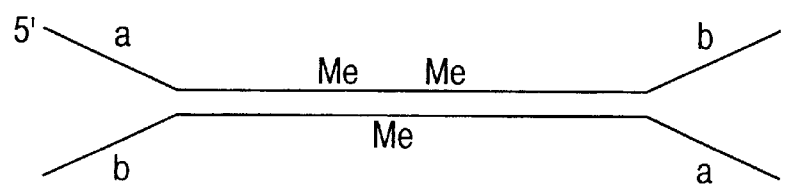

Adapters are then ligated to the fragments to obtain fragment-plus-adapter constructs. Linear or Y-shaped adapters may be employed. Y-shaped adapters are used in many preferred embodiments, but, in some cases, where Y-shaped adapters are illustrated, the methods can also be adapted to conventional linear adapters. Y-shaped adapters have been described (see Prashar, Y., and Weissman, S., *Proc. Natl. Acad Sci. USA*, 1996, 93:659–663). A Y-shaped adapter typically has an overhang on its 3'-end for ligation, and on the 5'-end, a stretch of noncomplementary sequence on the opposite strands, giving rise to its Y-shape (see FIGS. 1A and B). It is an advantage of the invention that, in preferred embodiments, the Y-shaped adapters allow for the synthesis of non-overlapping subsets of DNA. In typical embodiments, if the invention is carried out with conventional, linear primers, then the PCR-generated subsets will be partially overlapping, that is, some DNA sequences will be represented in more than one subset.

The fragment-plus adapter constructs are subjected to a PCR or to a single primer extension reaction in the presence of a primer complementary to at least a portion of the adapter at the 3'-end of the fragment-plus-adapter constructs and extending across the adapter ligation, and having at least one nucleotide overlap into the DNA fragment sequence. As used herein, a "polymerase chain reaction" includes conventional PCR, as well as modifications employing betaine, proof-editing polymerases, DMSO, and the like, and combinations thereof. Likewise, "rolling circle amplification" includes variants described by Hingorani and O'Donnell, cited above, and specifically encompasses modifications using a reconstituted bacterial polymerase III system including holoenzyme, helicase, clamp proteins, and clamp loading proteins (Bloom, L. B., et al., *J Biol. Chem.*, 1997, 272:27919–27930).

Figure 1C:
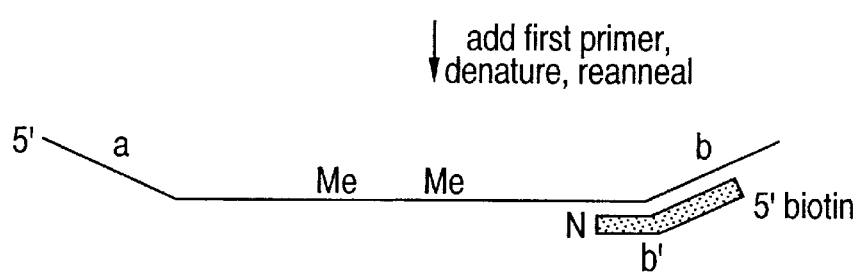
In FIG. 1C, a primer is annealed to the denatured fragment-plus-adapter construct for use in single primer extension, PCR or other DNA polymerase reaction. The 5'-end of the primer consists of a sequence complementary to the adapter region (b) and, at the 3'-end, the primer has one or more nucleotides (N) which must properly anneal to the fragment sequence in order for priming to occur. Therefore, only a subset of fragment sequences that are complementary to the nucleotide(s) N of the primer will be replicated. A capture moiety, in this case biotin, can be present to allow isolation of reaction products.
Figure 1D:
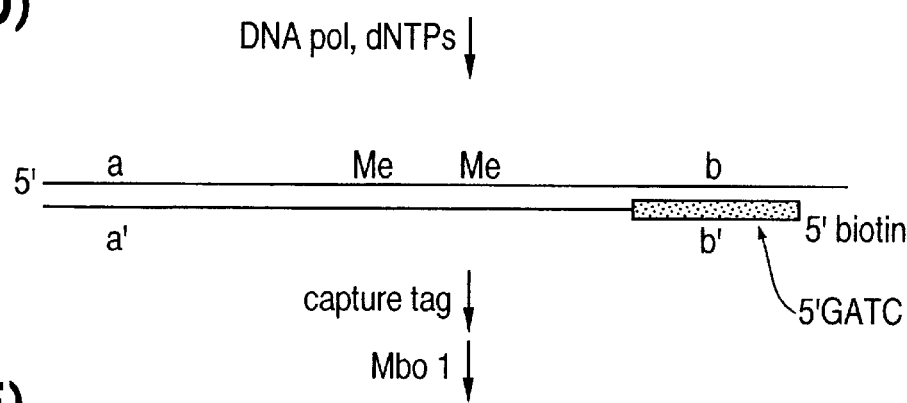
In FIG. 1D, extension of the primer by DNA polymerase generates a product, the 3'-end of which is complementary to the adapter region (a). Therefore, this DNA product can itself be replicated by use of a primer complementary to the sequence (a) in a primer extension, PCR, or other DNA polymerase reaction. Because of the Y-shaped adapters, the products of such replication reactions will be in non-overlapping subsets defined by the nucleotide (s) N of the primer. The presence of a restriction endonuclease recognition site in the adapter, in this case GATC (FIG. 1D), allows for the release of any DNA product following capture by the moiety as shown in FIG. 1E.
Figure 1E:
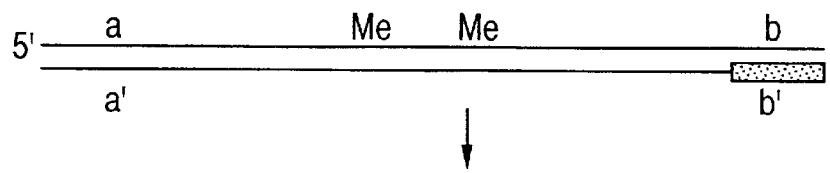
FIG. 1 is a diagram illustrating the addition of Y-shaped adapters to DNA fragments and generation of subsets reducing the complexity of the sequences.

In some cases, a tag at the 5'-end, and a restriction endonuclease recognition site at least about 6 nucleotides from the tag, are present to allow capture of a DNA product and subsequent release by cutting with the restriction endonuclease. In some embodiments, the annealed primer extends across the adapter ligation site one nucleotide into the DNA fragment sequence; in others, they extend two; and in others, more than two. The number of nucleotides, and the identity of the nucleotides that the primer extends across the adapter ligation site, determines the members of the subset to be amplified. The tag in many embodiments is biotin, illustrated in FIG. 1C.

In an alternative method for generating subsets, DNA samples are cut with a restriction endonuclease, such as Bsl1, that generates variable overhangs. That is, some of the bases in the recognition site can be of any two or more of the four possible bases G, A, T, or C. Adapters having overhangs complementary for this restriction endonuclease recognition site are ligated onto the fragments. Adapter overhangs having a unique sequence for the variable sites will only ligate to a subset of fragments that are complementary at those positions. Therefore, a subset of fragments will be replicated by a primer complementary to the adapter. By employing Y-shaped adapters, the subsets will be non-overlapping. Another advantage of this method is that it is a simple process to ligate adapters of one sequence at one end of the fragment and adapters of a second sequence at the other end of the fragment. If the adapters differ from each other in the primer annealing sequence of their non-complementary (Y-shaped) regions, then it is possible to amplify only one strand of the duplex adapter-fragment complex with the appropriate primer set in a PCR or other DNA polymerase reaction.

In a typical practice of a method of the invention, a subset of fragments are generated from one sample of a DNA or a mixture of DNAs, and these are methylated. The same subset is obtained from a second sample of DNA or mixture of DNAs, and these are not methylated. Mixing, denaturing and reannealing the methylated and unmethylated samples together generates hemimethylated heterohybrids, and, where a large number of DNA samples have been pooled together, most of the reannealed duplex DNA will be heterohybrids. The reannealing thus primarily results in perfectly matched heterohybrids or mismatched heterohybrids, depending upon the degree of polymorphism of the samples. In some cases, the mismatched heterohybrids are then selected by binding of MutS to the mismatch or subjected to MutSLH, which nicks any that contain the mismatched base pairs expected for regions of high polymorphism (see U.S. Pat. No. 5,556,750 to Modrich, et al., Cheung, V. G., et al., *Nature Genetics*, 1998, 18:225–230, and the references cited therein).

In the case where samples are treated with MutSLH, the nick that is generated in mismatched DNA is utilized to identify, isolate, amplify, or clone these fragments using a variety of methods that take advantage of the nick. In one case, a capture agent such as a biotin-tagged nucleotide is added onto the nick by terminal transferase or some other DNA polymerase and the nicked fragment is thereby isolated. Alternatively, the nicked strand can be removed by treatment with an exonuclease according to a published method (Nelson, S. F., et al., cited above). The surviving strand is then selected by DNA amplification or other methods. In another use of MutSLH nicked DNA, the 3'-OH of the nick serves as a primer for a DNA polymerase. Extension of the 3'-OH requires that the DNA polymerase utilize a duplex DNA template by a nick translation or strand displacement reaction. The newly synthesized DNA can be detected by the incorporation of a radioactively or fluorescently labelled nucleotide, or captured by the incorporation of a nucleotide appropriately tagged with a capture agent such as biotin. Also, extension of the nick where the Y-shaped adapter-fragment constructs of this invention are employed results in a DNA product which can be specifically replicated with unique primer sets in a PCR reaction or with a unique "splint oligonucleotide" in a rolling circle amplification. Referred to above, RCA is an isothermal amplification reaction in which a DNA polymerase extends a primer on a circular template (see Kornberg and Baker and other references cited above). The product consists of tandemly linked copies of the complementary sequence of the template.

In the case of RCA, the "splint oligonucleotide" is frequently a single-stranded sequence complementary to the ends of the DNA that results from extension of the nick such that denaturation of the DNA and annealing of the splint to the extended strand circularizes it. If the DNA is circularized such that its two ends are brought together at a nick, then the ends can be ligated together by DNA ligase forming a covalently closed circle. This DNA can then be amplified in an RCA. Another aspect of this invention is that DNA polymerase m holoenzyme derived from *E.coli* or other bacteria, including gram-positive and gram-negative bacteria, or related DNA polymerases from eukaryotes that have clamp (PCNA) and clamp loader (RFC) components (Kornberg and Baker, cited above) can be employed as the DNA polymerase in RCA. Use of DNA pol III is advantageous in many embodiments because pol III has a greater rate and processivity than other DNA polymerases and provides superior yield and ability to replicate long templates and templates having obstructions to DNA replication such as high GC content, or unfavorable secondary structure or sequence context. The *E. coli* dnaB and dnaC proteins or other helicases and the single-stranded DNA binding protein (SSB) can also be used to facilitate the reaction (Kornberg and Baker, cited above).

In another use of the nick generated in mismatched DNA by MutSLH, the mismatched DNA is discarded and the perfectly matched DNA can thereby be selectively amplified. For example, PCR primers, or a splint oligonucleotide in the case of RCA, can be used to amplify those DNAs not nicked by MutSLH whereas nicked DNA cannot provide an intact DNA template.

The methods employed in this invention depend on the isolation of heterohybrid DNA in which the two strands are derived from two different DNA samples. This can be accomplished by published methods (Nelson, et al., cited above). Improved procedures that do not require methylation of fragment DNA are included in this invention Sequences in the adapters are designed to allow selective cutting of homohybrid or heterohybrid DNA with restriction endonucleases. In some methods, the adapters contain two adjacent restriction enzyme recognition sites with specific methylation patterns such that heterohybrid and homohybrid DNAs can be distinguished by the ability of the methyl groups to block cutting by the restriction endonuclease. In other methods, partial restriction endonuclease recognition sequences are present in which the adapter contains mismatched bases. In this case heterohybrid and homohybrid DNAs can be distinguished by the elimination of the mismatches which allows restriction endonuclease to cut these sites.

EXAMPLES

Example 1.
Procedure for Creating cDNA or Genomic DNA Subsets

This example illustrates the use of PCR to amplify a subset of cDNA. The method can be used also for total genomic DNA or other mixtures of DNAs. The Y shaped adapters are designed two create "butterfly" ends on the construct (see FIG. 2). The Y type adaptors enable only one strand but not the other strand of the fragment to be amplified. Also, both strands can be amplified separately. This is useful when the fragment contains a mismatched base pair and it is desirable to amplify the strands separately. The Y shaped adapters also enable the amplified duplex to be sequenced. The PCR primers are designed so that their 5' end is complementary to adapter sequence, but 1–3 nucleotides at their 3' end (designated by "N" in FIG. 2) must base pair with the target DNA insert. The target DNA sequences that will be amplified are determined by the identity of the 3' terminal nucleotides of the PCR primers. Therefore, only a subset of sequences will be amplified and the complexity of the sample will be reduced.

In this example, cDNA was cut with a 4 nucleotide-recognizing restriction enzyme, Sau3AI. The restriction enzyme was inactivated after digestion was completed by treating it at 65 C. for 30 minutes. The digested DNA was then purified by phenol chloroform extraction. Y shaped adaptors were formed by annealing as follows: 1.3 nmol XS1, 1.3 nmol XS2, 5 mM Tris-HCl pH7.5 and 100 mM NaCl in 100 microliters volume at 94 C.×10 min, cool down to 37 C.×2 hrs, then 32 C.×2 hrs, 30 C.×2 Hrs, 28×2 Hrs, 25×2 Hrs and on ice. The fragments were then ligated to Y shaped adaptors as follows: cut cDNA 0. 1 micrograms, adaptor pair 0.2 micrograms/13 pmol, ligase 8u and 1×ligase buffer in 5 microliters at 16 C. overnight. A subset of the sequences was then amplified with a pair of PCR primers (see primer sequences below) in the following mixture: 2 microliters of 200-fold diluted ligated product from above, 2 ul of 2 micromolar each primer, 0.75 units AmpliTag Gold DNA Polymerase (Perkin Elmer), 2 mM each dNTP and 1×DNA polymerase buffer supplied by the manufacturer. The PCR was done in a Perkin Elmer Cetus Gene Amp PCR System 9600 with the program:

95 C., 4 min
five cycles
94 C., 30 sec
55 C., 30 sec
72 C., 30 sec
25 cycles
94 C., 30 sec
65 C., 30 sec
72 C., 30 sec
72 C., 5 min.

Figure 2:
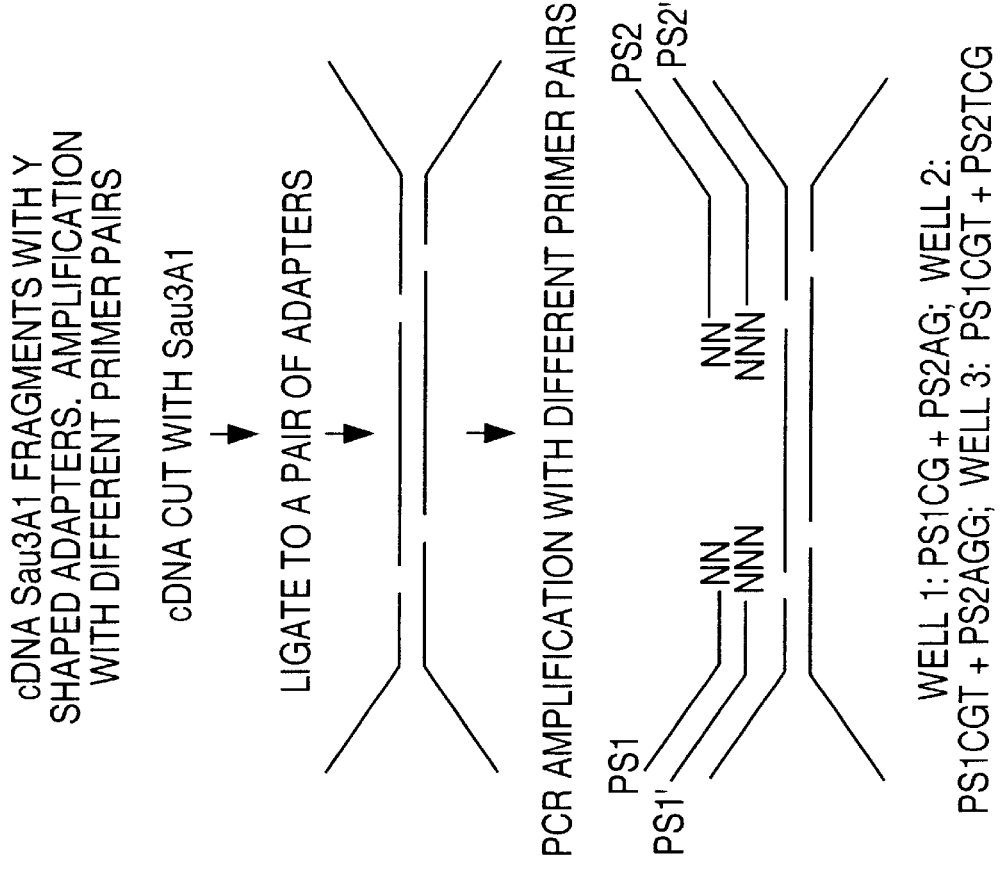
FIG. 2A shows cDNA Sau3A1 fragments with Y shaped adapters and amplification with different primer pairs.
FIG. 2B shows the results of amplification with three different primer pairs.
Figure 2:
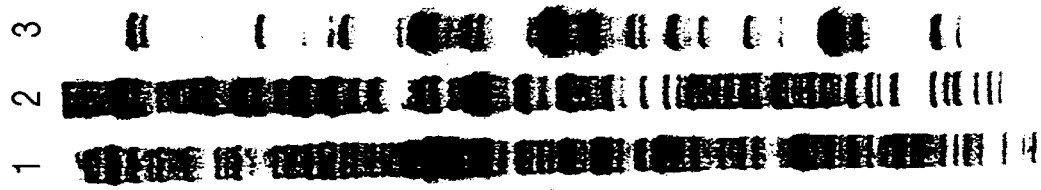

As indicated in FIG. 2, three different primer sets were used. Well number 1 contained a primer sequence which has C and G as the two 3' terminal nucleotides (designated PS1CG), and PS2AG which has A and Gas the terminal nucleotides. Wells 2 and 3 of FIG. 2 contained primer sets with different terminal nucleotides as indicated. As expected, the three PCR reactions produced different band patterns determined by which primer set was used.

Adaptor for Sau3AI cutting
XS1 (22 nt)
CGTCCGGCGCAGCGACGGTCAG SEQ. ID. NO:1
XS2 (29 nt)
GATCCTGACCGTCCGATCTCTGTCGCAGCG SEQ. ID. NO:1
PCR Primers (corresponding to above Sau3AI adaptors):
Set1:
PS1CG (28 nt)
CGTCCGGCGCAGCGACGGTCAGGATCCG SEQ. ID. NO:3
PS2AG (31 nt)
CGCTGCGACAGAGATGGACGGTCAGGATCAG SEQ. ID. NO:4
Set2:
PS1CGT (29 nt)
CGTCCGGCGCAGCGACGGTCAGGATCCGT SEQ. ID. NO:5
PS2AGG0 (32 nt)
CGCTGCGACAGAGATGGACGGTCAGGATCAGG SEQ. ID. NO:6
Set3:
PS1CGT (29 nt)
CGTCCGGCGCAGCGACGGTCAGGATCCGT SEQ. ID. NO:7
PS2TCG (32 nt)
CGCTGCGACAGAGATGGACGGTCAGGATCTCG SEQ. ID. NO:8

The above description is for the purpose of teaching the person of ordinary skill in the art how to practice the present invention, and it is not intended to detail all those obvious modifications and variations of it which will become apparent to the skilled worker upon reading the description. For example, there are numerous variations of steps in the overall procedures, and for preparing the probes. Variations in primers having larger overlap with DNA fragments and various amplification techniques, for example, have already been mentioned. Following selective isolation of duplex DNA, it could be transcribed with T7 or other appropriate RNA polymerase, and the RNA used as a direct probe, or reconverted into double-stranded DNA in some embodiments. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers, books and patents cited herein are expressly incorporated in their entireties by reference.

What is claimed is:

1. A method for selectively recovering heterohybrid DNA from a reannealed mixture of two DNA samples, wherein the heterohybrid DNA has one strand derived from a first sample, and one strand derived from a second sample, comprising:

(a) methylating both strands of the first sample but not the second sample with enzyme DAM methylase;

(b) methylating both samples with a methylase that protects all restriction sites recognized and cleaved by a restriction enzyme against cleavage by said restriction enzyme such that either strand of a duplex will be protected from cleavage by said restriction enzyme;

(c) ligating to both first and second samples Y-shaped adapters that have a first and second site for said restriction enzyme such that the upper strand of the first site and the lower strand of the second site are methylated in adapters ligated to the first sample and the lower strand of the first site and the upper strand of the second site are methylated in the second sample;

(d) denaturing, mixing, and reannealing the samples obtained in (c);

(e) cleaving the samples with restriction enzymes Dpn1 and Mbo1 to destroy all homohybrids; and (f) selectively recovering heterohybrid DNA so produced.

2. A method for selectively recovering homohybrid DNA from a reannealed mixture of a first and a second DNA sample, wherein the homohybrid DNA have two strands derived from the same sample, comprising:

(a) methylating both strands of the first sample but not the second sample with enzyme DAM methylase;

(b) methylating the samples with a methylase that protects all restriction sites recognized and potentially cleaved by a restriction enzyme against cleavage by said restriction enzyme such that either strand of a duplex will be protected from cleavage by said restriction enzyme;

(c) ligating to both first and second samples adapters that have first and second sites for said restriction enzyme such that the upper strand of the first site and the lower strand of the second site are methylated in adapters ligated to the first sample and the lower strand of the first site and the upper strand of the second site are methylated in the second sample;

(d) denaturing, mixing, and reannealing the samples obtained in (c);

(e) cleaving the methylated and unmethylated samples with said restriction enzyme to destroy heterohybrids; and (f) selectively recovering homohybrid DNA so produced.

3. A method for selectively recovering duplex DNA from a reannealed mixture of two samples, wherein the heterohybrid duplex DNA has one strand derived from one sample, and one strand derived from the other sample, comprising:

(a) attaching an adapter containing two inverted copies of a first asymmetric restriction site and two inverted copies of a second asymmetric restriction site to first and second samples;

(b) enzymatically methylating all first asymmetric restriction sites in the first sample and all second asymmetric restriction sites in the second sample;

(c) denaturing, mixing, and reannealing to obtain a sample mixture;

(d) subjecting the mixture to an incubation with an enzyme that cleaves the second asymmetric restriction sites to destroy DNA duplexes wherein both strands are derived from the first sample, and subjecting the mixture to an incubation with an enzyme that cleaves the first asymmetric restriction sites to destroy DNA duplexes wherein both strands are derived from the second sample; and (e) selectively recovering heterohybrid duplexes having one strand from each sample so produced.

4. A method according to claims 1, 2, or 3 wherein the 3'-ends of the molecules are blocked by addition of dideoxynucleotides before further amplification and analysis.

5. A method for selectively recovering a set of heterohybrid duplex DNA from a reannealed mixture of two DNA fragment samples, wherein the set contains duplexes having one strand derived from a first sample and one strand derived from a second sample, comprising:

(a) ligating to the fragments of the first and second samples first and second Y-shaped adapters that have a short arm terminating with a 3'-hydroxyl and a longer arm terminating with a 5'-phosphate wherein the short arm of the first Y-shaped adaptor ligated to the first sample is complementary to the longer arm of the second Y shaped adaptor ligated to the second sample and vice versa to provide fragment-plus-adapter constructs;

(b) mixing, denaturing, and reannealing the fragment-plus-adapter constructs; and (c) amplifying heterohybrid duplexes having one strand from the first sample and one strand derived from the second sample so obtained using primers or splints having a sequence identical to the distal part of the longer arms of the Y-shaped adapters.

6. A method for selectively recovering a set of duplex DNA from a reannealed mixture of two halves of a DNA fragment sample, wherein the set contains duplexes containing a mismatched nucleotide pair, comprising:

(a) ligating half of the fragment sample to one Y-shaped adapter, and the other half of the fragment sample to another Y-shaped adapter, to obtain fragment-plus-adapter constructs that have different sequences in their single-stranded arms;

(b) methylating with DAM methylase one of the halves of the fragment samples ligated to one of the Y-shaped adapters;

(c) mixing the two fragment-plus-adapter construct halves of the sample together and denaturing and reannealing the mixture to form reannealed products;

(d) treating the reannealed products of step (c) with MutSLH to produce nicks and extending the nicks so produced with DNA polymerase or with a combination of DNA polymerase III holoenzyme and another DNA polymerase having strand displacement or nick translation capacity;

(e) denaturing duplex DNA obtained in step (d);

(f) circularizing the denatured duplex DNA such that its two ends are brought together with a splint oligonucleotide having a sequence with one end complementary to an arm of one Y-shaped adapter and the other side complementary to the other Y-shaped adapter; and (g) performing a rolling circle amplification using DNA polymerase III holoenzyme or other DNA polymerase, or a combination of two or more DNA polymerases to form circles only from homoduplexes that had been nicked by MutSLH.

7. A method for selectively recovering a set of duplex DNA from a reannealed mixture of two DNA fragment samples, wherein the set contains heterohybrid duplexes having one strand derived from a first sample and one strand derived from a second sample, wherein the set of duplex DNA contains a mismatched nucleotide pair, comprising:

(a) ligating the first fragment sample to one of two Y-shaped adapters having different sequences in their single-stranded arms, and the second fragment sample to the other Y-shaped adapter to obtain fragment-plus-adapter constructs;

(b) methylating with DAM methylase one of the fragment samples ligated to one of the Y-shaped adapters;

(c) mixing, denaturing, and reannealing the two fragment-plus-adapter constructs from the first and second samples together;

(d) treating the reannealed constructs of step (c) with MutSLH to form nicks and extending the nicks so produced with a DNA polymerase having strand displacement or nick translation capability;

(e) denaturing duplex DNA obtained in step (d);

(f) circularizing the denatured DNA such that its two ends are brought together with a splint oligonucleotide having a sequence with one end complementary to an arm of the first Y-adapter and another sequence complementary to the second Y-adapter; and (g) performing a rolling circle amplification that forms circles only from heteroduplexes that had been nicked by MutSLH.

8. A method for selectively recovering heterohybrid duplex DNA from a reannealed mixture of two DNA samples, wherein the heterohybrid duplex DNA has one strand derived from a first sample, and one strand derived from a second sample, comprising:

(a) ligating to the first sample a first Y-shaped adapter that has a first site that encodes a complete recognition sequence for a restriction endonuclease, and a second site that differs from the complete recognition site for the restriction endonuclease by one or more bases and therefore is nonfunctional as a cutting site;

(b) ligating to the second sample a second Y-shaped adapter that has a first site that differs from the complete recognition sequence of the restriction endonuclease by one or more bases and a second site that is a complete recognition sequence of the restriction endonuclease;

(c) mixing, denaturing, and reannealing the samples obtained in (a) and (b); and (d) cutting the reannealed DNA of step (c) with the restriction endonuclease and selectively recovering the heterohybrid DNA so produced.

9. A method for selectively recovering from a reannealed mixture of DNA fragment sample A and DNA fragment sample B a set of heterohybrids of samples A and B or a set of homohybrids of sample A, or a set of homohybrids of sample B, wherein the set contains a mismatched nucleotide pair, comprising:

(a) ligating a first half of sample A to a first Y-shaped adapter having different sequences in its single stranded arms, and a second half of sample A to a second Y-shaped adapter having different sequences in its single stranded arms from those of the first Y-shaped adapter to obtain fragment-plus-adapter constructs;

(b) methylating with DAM methylase one of the two halves of fragment-plus-adapter constructs of sample A;

(c) mixing the two halves of the fragment-plus-adapter constructs of sample A together;

(d) ligating a first half of sample B to a third Y-shaped adapter, and a second half of sample B to a fourth Y-shaped adapter to obtain fragment-plus-adapter constructs;

(e) methylating with DAM methylase one of the two halves of fragment-plus-adapter constructs of sample B;

(f) mixing the two halves of the fragment-plus-adapter constructs of sample B together;

(g) mixing, denaturing, and reannealing the fragment-plus-adapter constructs from sample A obtained in step (c) and the fragment-plus-adapter constructs from sample B obtained in step (f);

(h) treating the mixture of step (g) with MutSLH to form nicks and extending the nicks so produced with a DNA polymerase having strand displacement or nick translation capability;

(i) denaturing duplex DNA obtained in step (h);

(j) circularizing a product of step (i) with a splint oligonucleotide having a sequence with one end complementary to an arm of one Y-shaped adapter, and another sequence complementary to an arm of another Y-shaped adapter; and (k) performing a rolling circle amplification to amplify strands that formed circles in step (j) to yield either mismatched heteroduplexes of samples A and B, or mismatched homoduplexes of sample A, or mismatched homoduplexes of sample B.

* * * * *

UNITED STATES PATENT AND TRADEMARK OFFICE
CERTIFICATE OF CORRECTION

PATENT NO.    : 6,372,434 B1                                                Page 1 of 1
DATED         : April 16, 2002
INVENTOR(S)   : Sherman Weissman et al.

It is certified that error appears in the above-identified patent and that said Letters Patent is hereby corrected as shown below:

<u>Title page,</u>
Item [73], add the following:
-- Yale University, New Haven, CT --

Signed and Sealed this

First Day of April, 2003

JAMES E. ROGAN
*Director of the United States Patent and Trademark Office*

SEQUENCE LISTING

<160> NUMBER OF SEQ ID NOS: 19

<210> SEQ ID NO 1
<211> LENGTH: 1793
<212> TYPE: DNA
<213> ORGANISM: Homo sapiens

<400> SEQUENCE: 1

| | | | | | |
|---|---|---|---|---|---|
| gttgagtcaa | tgtgtccccc | tcttgttcct | agggtgcggg | cttcatggcc | ttctcctcca | 60 |
| ggaagctcca | cctgatcatg | tcctgggtgg | atatccagcc | cccatagttc | agggcctact | 120 |
| agcagctgct | agatcttgaa | ctccaggagc | gccccacgcc | ttgggagctt | ggcatgggct | 180 |
| aaatactccc | ccatttgtta | aatggggtcc | tgaaacctga | ccagggaaga | cgggataaag | 240 |
| tagccatggg | tcatcgcagc | cccttttgaag | ccgggcctgg | ccacccaaag | gcaactcagg | 300 |
| ggtggagact | gaggcctcag | gagaagcccc | cactagaatg | ctctctgccc | ctcccttcca | 360 |
| gattaaccaa | aacctgctaa | ttgtggaagc | cctcggcatg | ctcccctccc | ccacagcctc | 420 |
| ttcctcccctt | ccctcccctc | cccttccat | ccgaatgata | aaggcccag | cccgcctgcc | 480 |
| ccagcccggc | ctcaggtccc | ggccctgcct | tctacactgc | ccaccgccc | tgcaccctcc | 540 |
| acccggccag | gccctgccc | acgctgtcta | ccgtcccgca | tggggccctg | cagcggctcc | 600 |
| cgcctggggc | cccagaggc | agagtcgccc | tcccagcccc | ctaagaggag | gaagaagagg | 660 |
| tacctgcgac | atgacaagcc | cccctacacc | tacttggcca | tgatcgcctt | ggtgattcag | 720 |
| gccgctccct | cccgcagact | gaagctggcc | cagatcatcc | gtcaggtcca | ggccgtgttc | 780 |
| cccttcttca | gggaagacta | cgagggctgg | aaagactcca | ttcgccacaa | cctttcctcc | 840 |
| aaccgatgct | tccgcaaggt | gcccaaggac | cctgcaaagc | cccaggccaa | gggcaacttc | 900 |
| tgggcggtcg | acgtgagcct | gatcccagct | gaggcgctcc | ggctgcagaa | caccgccctg | 960 |
| tgccggcgct | ggcagaacgg | aggtgcgcgt | ggagccttcg | ccaaggacct | gggcccctac | 1020 |
| gtgctgcacg | gccggccata | ccggccgccc | agtccccgc | caccacccag | tgagggcttc | 1080 |
| agcatcaagt | ccctgctagg | agggtccggg | gagggggcac | cctggccggg | gctagctcca | 1140 |
| cagagcagcc | cagttcctgc | aggcacaggg | aacagtgggg | aggaggcggt | gcccacccca | 1200 |
| ccccttccct | cttctgagag | gcctctgtgg | cccctctgcc | ccttcctgg | ccccacgaga | 1260 |
| gtggaggggg | agactgtgca | gggggagcc | atcgggccct | caaccctctc | cccagagcct | 1320 |
| agggcctggc | ctctccactt | actgcagggc | accgcagttc | ctggggacg | tccagcggg | 1380 |
| ggacacaggg | cctccctctg | ggggcagctg | cccacctcct | acttgcctat | ctacactccc | 1440 |
| aatgtggtaa | tgcccttggc | accaccaccc | acctcctgtc | cccagtgtcc | gtcaaccagc | 1500 |
| cctgcctact | gggggtggc | ccctgaaacc | cgagggcccc | cagggctgct | ctgcgatcta | 1560 |
| gacgccctct | tccaagggt | gccacccaac | aaaagcatct | acgacgtttg | ggtcagccac | 1620 |
| cctcgggacc | tggcggcccc | tggcccaggc | tggctgctct | cctggtgcag | cctgtgaggc | 1680 |
| tcttaagaca | ggggccgctc | ctccctcccg | ctcccacccc | caccttgttg | acagggagca | 1740 |
| agggaggcgg | ctgtctgcga | cacagcagct | cgaaaaccag | gcagagcttg | ttg | 1793 |

<210> SEQ ID NO 2
<211> LENGTH: 365
<212> TYPE: PRT
<213> ORGANISM: Homo sapiens

<400> SEQUENCE: 2

-continued

```
Met Gly Pro Cys Ser Gly Ser Arg Leu Gly Pro Pro Glu Ala Glu Ser
 1               5                  10                  15

Pro Ser Gln Pro Pro Lys Arg Arg Lys Lys Arg Tyr Leu Arg His Asp
            20                  25                  30

Lys Pro Pro Tyr Thr Tyr Leu Ala Met Ile Ala Leu Val Ile Gln Ala
        35                  40                  45

Ala Pro Ser Arg Arg Leu Lys Leu Ala Gln Ile Ile Arg Gln Val Gln
    50                  55                  60

Ala Val Phe Pro Phe Phe Arg Glu Asp Tyr Glu Gly Trp Lys Asp Ser
65                  70                  75                  80

Ile Arg His Asn Leu Ser Ser Asn Arg Cys Phe Arg Lys Val Pro Lys
                85                  90                  95

Asp Pro Ala Lys Pro Gln Ala Lys Gly Asn Phe Trp Ala Val Asp Val
            100                 105                 110

Ser Leu Ile Pro Ala Glu Ala Leu Arg Leu Gln Asn Thr Ala Leu Cys
        115                 120                 125

Arg Arg Trp Gln Asn Gly Gly Ala Arg Gly Ala Phe Ala Lys Asp Leu
    130                 135                 140

Gly Pro Tyr Val Leu His Gly Arg Pro Tyr Arg Pro Ser Pro Pro
145                 150                 155                 160

Pro Pro Pro Ser Glu Gly Phe Ser Ile Lys Ser Leu Leu Gly Gly Ser
            165                 170                 175

Gly Glu Gly Ala Pro Trp Pro Gly Leu Ala Pro Gln Ser Ser Pro Val
            180                 185                 190

Pro Ala Gly Thr Gly Asn Ser Gly Glu Glu Ala Val Pro Thr Pro Pro
        195                 200                 205

Leu Pro Ser Ser Glu Arg Pro Leu Trp Pro Leu Cys Pro Leu Pro Gly
    210                 215                 220

Pro Thr Arg Val Glu Gly Glu Thr Val Gln Gly Gly Ala Ile Gly Pro
225                 230                 235                 240

Ser Thr Leu Ser Pro Glu Pro Arg Ala Trp Pro Leu His Leu Leu Gln
                245                 250                 255

Gly Thr Ala Val Pro Gly Gly Arg Ser Ser Gly Gly His Arg Ala Ser
            260                 265                 270

Leu Trp Gly Gln Leu Pro Thr Ser Tyr Leu Pro Ile Tyr Thr Pro Asn
    275                 280                 285

Val Val Met Pro Leu Ala Pro Pro Thr Ser Cys Pro Gln Cys Pro
        290                 295                 300

Ser Thr Ser Pro Ala Tyr Trp Gly Val Ala Pro Glu Thr Arg Gly Pro
305                 310                 315                 320

Pro Gly Leu Leu Cys Asp Leu Asp Ala Leu Phe Gln Gly Val Pro Pro
                325                 330                 335

Asn Lys Ser Ile Tyr Asp Val Trp Val Ser His Pro Arg Asp Leu Ala
            340                 345                 350

Ala Pro Gly Pro Gly Trp Leu Leu Ser Trp Cys Ser Leu
        355                 360                 365

<210> SEQ ID NO 3
<211> LENGTH: 477
<212> TYPE: PRT
<213> ORGANISM: Homo sapiens

<400> SEQUENCE: 3

Val Ala Met Ile Asn Ala Cys Ile Asp Ser Met Ser Ser Ile Leu Pro
```

-continued

```
  1               5                  10                 15
Phe Thr Pro Pro Val Val Lys Arg Leu Leu Gly Trp Lys Lys Ser Ala
            20                  25                 30
Gly Gly Ser Gly Gly Ala Gly Gly Glu Gln Asn Gly Gln Glu Glu
            35              40              45
Lys Trp Cys Glu Lys Ala Val Lys Ser Leu Val Lys Lys Leu Lys Lys
        50              55              60
Thr Gly Arg Leu Asp Glu Leu Glu Lys Ala Ile Thr Thr Gln Asn Cys
 65              70              75              80
Asn Thr Lys Cys Val Thr Ile Pro Ser Thr Cys Ser Glu Ile Trp Gly
                85              90              95
Leu Ser Thr Pro Asn Thr Ile Asp Gln Trp Asp Thr Thr Gly Leu Tyr
            100             105             110
Ser Phe Ser Glu Gln Thr Arg Ser Leu Asp Gly Arg Leu Gln Val Ser
            115             120             125
His Arg Lys Gly Leu Pro His Val Ile Tyr Cys Arg Leu Trp Arg Trp
            130             135             140
Pro Asp Leu His Ser His His Glu Leu Lys Ala Ile Glu Asn Cys Glu
145             150             155             160
Tyr Ala Phe Asn Leu Lys Lys Asp Glu Val Cys Val Asn Pro Tyr His
                165             170             175
Tyr Gln Arg Val Glu Thr Pro Val Leu Pro Pro Val Leu Val Pro Arg
            180             185             190
His Thr Glu Ile Leu Thr Glu Leu Pro Pro Leu Asp Asp Tyr Thr His
            195             200             205
Ser Ile Pro Glu Asn Thr Asn Phe Pro Ala Gly Ile Glu Pro Gln Ser
210             215             220
Asn Tyr Ile Pro Glu Thr Pro Pro Gly Tyr Ile Ser Glu Asp Gly
225             230             235             240
Glu Thr Ser Asp Gln Gln Leu Asn Gln Ser Met Asp Thr Gly Ser Pro
                245             250             255
Ala Glu Leu Ser Pro Thr Thr Leu Ser Pro Val Asn His Ser Leu Asp
            260             265             270
Leu Gln Pro Val Thr Tyr Ser Glu Pro Ala Phe Trp Cys Ser Ile Ala
            275             280             285
Tyr Tyr Glu Leu Asn Gln Arg Val Gly Glu Thr Phe His Ala Ser Gln
290             295             300
Pro Ser Leu Thr Val Asp Gly Phe Thr Asp Pro Ser Asn Ser Glu Arg
305             310             315             320
Phe Cys Leu Gly Leu Leu Ser Asn Val Asn Arg Asn Ala Thr Val Glu
            325             330             335
Met Thr Arg Arg His Ile Gly Arg Gly Val Arg Leu Tyr Tyr Ile Gly
            340             345             350
Gly Glu Val Phe Ala Glu Cys Leu Ser Asp Ser Ala Ile Phe Val Gln
            355             360             365
Ser Pro Asn Cys Asn Gln Arg Tyr Gly Trp His Pro Ala Thr Val Cys
        370             375             380
Lys Ile Pro Pro Gly Cys Asn Leu Lys Ile Phe Asn Asn Gln Glu Phe
385             390             395             400
Ala Ala Leu Leu Ala Gln Ser Val Asn Gln Gly Phe Glu Ala Val Tyr
            405             410             415
Gln Leu Thr Arg Met Cys Thr Ile Arg Met Ser Phe Val Lys Gly Trp
            420             425             430
```

-continued

```
Gly Ala Glu Tyr Arg Arg Gln Thr Val Thr Ser Thr Pro Cys Trp Ile
        435                 440                 445
Glu Leu His Leu Asn Gly Pro Leu Gln Trp Leu Asp Lys Val Leu Thr
    450                 455                 460
Gln Met Gly Ser Pro Ser Val Arg Cys Ser Ser Met Ser
465                 470                 475

<210> SEQ ID NO 4
<211> LENGTH: 8
<212> TYPE: DNA
<213> ORGANISM: Homo sapiens

<400> SEQUENCE: 4 tgtkkatt                                                                8

<210> SEQ ID NO 5
<211> LENGTH: 18
<212> TYPE: DNA
<213> ORGANISM: Homo sapiens

<400> SEQUENCE: 5
ctggaaagac tccattcg                                                    18

<210> SEQ ID NO 6
<211> LENGTH: 19
<212> TYPE: DNA
<213> ORGANISM: Homo sapiens

<400> SEQUENCE: 6
cacagaggcc tctcagaag                                                   19

<210> SEQ ID NO 7
<211> LENGTH: 18
<212> TYPE: DNA
<213> ORGANISM: Homo sapiens

<400> SEQUENCE: 7
cccccttcca tccgaatg                                                    18

<210> SEQ ID NO 8
<211> LENGTH: 19
<212> TYPE: DNA
<213> ORGANISM: Homo sapiens

<400> SEQUENCE: 8
gagctgctgt gtcgcagac                                                   19

<210> SEQ ID NO 9
<211> LENGTH: 79
<212> TYPE: DNA
<213> ORGANISM: Artificial Sequence
<220> FEATURE:
<223> OTHER INFORMATION: flag primer

<400> SEQUENCE: 9
ggatcctaat acgactcact atagggagac caccatggac tacaaggacg acgatgacaa     60
ggggccctgc agcggctcc                                                  79

<210> SEQ ID NO 10
<211> LENGTH: 81
<212> TYPE: DNA
<213> ORGANISM: Artificial Sequence
```

```
<220> FEATURE:
<223> OTHER INFORMATION: flag primer

<400> SEQUENCE: 10
ggatcctaat acgactcact atagggagac caccatggac tacaaggacg acgatgacaa    60 gcccttcct ggccccacga g                                               81

<210> SEQ ID NO 11
<211> LENGTH: 31
<212> TYPE: DNA
<213> ORGANISM: Homo sapiens

<400> SEQUENCE: 11
tatgcggccg ccaccatggg gccctgcagc g                                   31

<210> SEQ ID NO 12
<211> LENGTH: 30
<212> TYPE: DNA
<213> ORGANISM: Homo sapiens

<400> SEQUENCE: 12
tatgcggccg cgagctgctg tgtcgcagac                                     30

<210> SEQ ID NO 13
<211> LENGTH: 7
<212> TYPE: DNA
<213> ORGANISM: Homo sapiens

<400> SEQUENCE: 13 rymaaya                                                              7

<210> SEQ ID NO 14
<211> LENGTH: 22
<212> TYPE: DNA
<213> ORGANISM: Homo sapiens

<400> SEQUENCE: 14
tagtaaacac tctatcaatt gg                                             22

<210> SEQ ID NO 15
<211> LENGTH: 20
<212> TYPE: DNA
<213> ORGANISM: Homo sapiens

<400> SEQUENCE: 15
gtccagtatc gtttacagcc                                                20

<210> SEQ ID NO 16
<211> LENGTH: 21
<212> TYPE: DNA
<213> ORGANISM: Homo sapiens

<400> SEQUENCE: 16
cggattgtgt attggctgta c                                              21

<210> SEQ ID NO 17
<211> LENGTH: 21
<212> TYPE: DNA
<213> ORGANISM: Homo sapiens

<400> SEQUENCE: 17
cggattctgt atcggctgta c                                              21
```

<210> SEQ ID NO 18
<211> LENGTH: 55
<212> TYPE: DNA
<213> ORGANISM: Homo sapiens

<400> SEQUENCE: 18
tatctgctgc cctaaaatgt gtattccatg gaaatgtctg cccttctctc cgtac     55

<210> SEQ ID NO 19
<211> LENGTH: 518
<212> TYPE: PRT
<213> ORGANISM: Xenopus laevis

<400> SEQUENCE: 19

Met Arg Asp Pro Ser Ser Leu Tyr Ser Gly Phe Pro Ala Gly Ser Gln
 1               5                  10                  15

Tyr Glu Ser Val Glu Pro Pro Ser Leu Ala Leu Leu Ser Ser Ile Asp
                20                  25                  30

Gln Glu Gln Leu Pro Val Ala Thr Gly Gln Ser Tyr Asn His Ser Val
            35                  40                  45

Gln Pro Trp Pro Gln Pro Trp Pro Pro Leu Ser Leu Tyr Arg Glu Gly
        50                  55                  60

Gly Thr Trp Ser Pro Asp Arg Gly Ser Met Tyr Gly Leu Ser Pro Gly
65                  70                  75                  80

Thr His Glu Gly Ser Cys Thr His Thr His Glu Gly Pro Lys Asp Ser
                85                  90                  95

Met Ala Gly Asp His Thr Arg Ser Arg Lys Ser Lys Lys Asn Tyr
                100                 105                 110

His Arg Tyr Tyr Lys Pro Pro Tyr Ser Tyr Leu Ala Met Ile Ala Leu
            115                 120                 125

Val Ile Gln Asn Ser Pro Glu Lys Arg Leu Lys Leu Ser Gln Ile Leu
        130                 135                 140

Lys Glu Val Ser Thr Leu Phe Pro Phe Phe Asn Gly Asp Tyr Met Gly
145                 150                 155                 160

Trp Lys Asp Ser Ile Arg His Asn Leu Ser Ser Ser Asp Cys Phe Lys
                165                 170                 175

Lys Ile Leu Lys Asp Pro Gly Lys Pro Gln Ala Lys Gly Asn Phe Trp
            180                 185                 190

Thr Val Asp Val Ser Arg Ile Pro Leu Asp Ala Met Lys Leu Gln Asn
        195                 200                 205

Thr Ala Leu Thr Arg Gly Gly Ser Asp Tyr Phe Val Gln Asp Leu Ala
    210                 215                 220

Pro Tyr Ile Leu His Asn Tyr Lys Tyr Glu His Asn Ala Gly Ala Tyr
225                 230                 235                 240

Gly His Gln Met Pro Pro Ser His Ala Arg Ser Leu Ser Leu Ala Glu
                245                 250                 255

Asp Ser Gln Gln Thr Asn Thr Gly Gly Lys Leu Asn Thr Ser Phe Met
            260                 265                 270

Ile Asp Ser Leu Leu His Asp Leu Gln Glu Val Asp Leu Pro Asp Ala
        275                 280                 285

Ser Arg Asn Leu Glu Asn Gln Arg Ile Ser Pro Ala Val Ala Met Asn
    290                 295                 300

Asn Met Trp Ser Ser Ala Pro Leu Leu Tyr Thr His Ser Lys Pro Thr
305                 310                 315                 320

Arg Asn Ala Arg Ser Pro Gly Leu Ser Thr Ile His Ser Thr Tyr Ser

-continued

|  |  |  | 325 |  |  |  | 330 |  |  |  | 335 |  |
|---|---|---|---|---|---|---|---|---|---|---|---|---|
| Ser | Ser | Ser | Ser | Ser | Ile | Ser | Thr | Ile | Ser | Pro | Val | Gly | Phe | Gln | Lys |
|  |  |  | 340 |  |  |  | 345 |  |  |  | 350 |  |
| Glu | Gln | Glu | Lys | Ser | Gly | Arg | Gln | Thr | Gln | Arg | Val | Gly | His | Pro | Ile |
|  |  |  | 355 |  |  |  | 360 |  |  |  | 365 |  |
| Lys | Arg | Ser | Arg | Glu | Asp | Asp | Asp | Cys | Ser | Thr | Thr | Ser | Ser | Asp | Pro |
|  |  |  | 370 |  |  |  | 375 |  |  |  | 380 |  |
| Asp | Thr | Gly | Asn | Tyr | Ser | Pro | Ile | Glu | Pro | Pro | Lys | Lys | Met | Pro | Leu |
| 385 |  |  |  |  |  | 390 |  |  |  | 395 |  |  |  | 400 |
| Leu | Ser | Leu | Asp | Leu | Pro | Thr | Ser | Tyr | Thr | Lys | Ser | Val | Ala | Pro | Asn |
|  |  |  | 405 |  |  |  | 410 |  |  |  | 415 |  |
| Val | Val | Ala | Pro | Pro | Ser | Val | Leu | Pro | Phe | Phe | His | Phe | Pro | Arg | Phe |
|  |  |  | 420 |  |  |  | 425 |  |  |  | 430 |  |
| Thr | Tyr | Tyr | Asn | Tyr | Gly | Pro | Ser | Pro | Tyr | Met | Thr | Pro | Pro | Tyr | Trp |
|  |  |  | 435 |  |  |  | 440 |  |  |  | 445 |  |
| Gly | Phe | Pro | His | Pro | Thr | Asn | Ser | Gly | Gly | Asp | Ser | Pro | Arg | Gly | Pro |
|  |  |  | 450 |  |  |  | 455 |  |  |  | 460 |  |
| Gln | Ser | Pro | Leu | Asp | Leu | Asp | Asn | Met | Leu | Arg | Ala | Met | Pro | Pro | Asn |
| 465 |  |  |  |  |  | 470 |  |  |  | 475 |  |  |  | 480 |
| Lys | Ser | Val | Phe | Asp | Val | Leu | Thr | Ser | His | Pro | Gly | Asp | Leu | Val | His |
|  |  |  | 485 |  |  |  | 490 |  |  |  | 495 |  |
| Pro | Ser | Phe | Leu | Ser | Gln | Cys | Leu | Gly | Ser | Ser | Gly | Ser | Pro | Tyr | Pro |
|  |  |  | 500 |  |  |  | 505 |  |  |  | 510 |  |
| Ser | Arg | Gln | Gly | Leu | Met |
|  |  |  | 515 |  |  |